United States Patent
Ollilainen et al.

(10) Patent No.: US 9,192,348 B2
(45) Date of Patent: Nov. 24, 2015

(54) METHOD AND SYSTEM FOR AUTOMATED DETECTION OF TISSUE INTERIOR TO A MAMMALIAN RIBCAGE FROM AN IN VIVO IMAGE

(71) Applicant: PerkinElmer Cellular Technologies Germany GmbH, Tallinn (EE)

(72) Inventors: Olavi Ollilainen, Tallinn (EE); Peet Kask, Harju maakond (EE)

(73) Assignee: PerkinElmer Cellular Technologies Germany GmbH, Tallinn (ES)

( * ) Notice: Subject to any disclaimer, the term of this patent is extended or adjusted under 35 U.S.C. 154(b) by 134 days.

(21) Appl. No.: 14/162,693

(22) Filed: Jan. 23, 2014

(65) Prior Publication Data
US 2015/0201896 A1  Jul. 23, 2015

(51) Int. Cl.
*A61B 6/00* (2006.01)

(52) U.S. Cl.
CPC ............... *A61B 6/5217* (2013.01); *A61B 6/466* (2013.01); *A61B 6/469* (2013.01); *A61B 6/505* (2013.01); *A61B 6/508* (2013.01); *A61B 6/563* (2013.01)

(58) Field of Classification Search
CPC ........ A61B 6/466; A61B 6/469; A61B 6/505; A61B 6/508; A61B 6/5217; A61B 6/563
See application file for complete search history.

(56) References Cited

U.S. PATENT DOCUMENTS

2008/0107318 A1  5/2008  Kiraly

FOREIGN PATENT DOCUMENTS

WO  WO-2009/101560 A2  8/2009

OTHER PUBLICATIONS

Ballard, Dana H., Model-Directed Detection of Ribs in Chest Radiographs, Computer Science Department, University of Rochester, 24 pages (1978).
de Bruijne, Marleen and Nielsen, Mads, Multi-object Segmentation Using Shape Particles, IPMI, LNCS 3565:762-773 (2005).
International Search Report for PCT/IB2014/000585, Oct. 14, 2014, 4 pages.
Khmelinskii, A. et al., Atlas-Based Organ & Bone Approximation for Ex-Vivo μMRI Mouse Data: A Pilot Study, IEEE ISBI, 1197-1200 (2010).
Klinder, T. et al., Automated Model-Based Rib Cage Segmentation and Labeling in CT Images, MICCA, Part II, LNCS 4792:195-202 (2007).
Lee, J. and Reeves, A. P., Segmentation of Individual Ribs from Low-dose Chest CT, Medical Imaging, 7624:J1-J8 (2010).
Maier, F. et al., Automatic Liver Segmentation Using the Random Walker Algorithm, Universität Karlsruhe (TH), Siemens Medical Solutions, Forchheim, Friedrich-Alexander University, Erlangen-Nuremberg, RWTH Aachen University, 6 pages. (2008).

(Continued)

*Primary Examiner* — Michael Rozanski
(74) *Attorney, Agent, or Firm* — Choate, Hall & Stewart LLP

(57) ABSTRACT

Described herein are systems and methods for efficient and accurate, automated detection of a region of interest interior to the ribcage from an in vivo mammalian image. It is found that efficient, automated identification of the region of interest interior to the ribcage can be achieved by the use of both a bone distance mask and a surface distance mask. The technique solves the problem of accurate and fast identification of the region of interest for a wide range of sizes and shapes of mammals, e.g., small mammals such as mice.

17 Claims, 12 Drawing Sheets

(56) References Cited

OTHER PUBLICATIONS

Staal, J. et al, Automatic rib segmentation and labeling in computed tomography scans using a general framework for detection, recognition and segmentation of objects in volumetric data, Medical Image Analysis 11:35-46 (2007).

Staal, J. et al., Automatic Rib Segmentation in CT Data, CVAMIA-MMBIA, LNCS 3117:193-204 (2004).

Sun, S. et al., Automated 3-D Segmentation of Lungs With Lung Cancer in CT Data Using a Novel Robust Active Shape Model Approach, IEEE Transactions on Medical Imaging, 31(2):449-460 (2012).

Wang, H. et al., Estimation of Mouse Organ Locations Through Registration of a Statistical Mouse Atlas With Micro-CT Images, IEEE Transactions on Medical Imaging, 31(1):88-102 (2012).

Wildeman, M. H. et al., 2D/3D Registration of Micro-CT Data to Multi-View Photographs Based on a 3D Distance Map, Biomedical Imaging, IEEE International Symposium ON, 987-990 (2009).

Written Opinion for PCT/IB2014/000585, Oct. 14, 2014, 6 pages.

Wu, D. et al, A Learning Based Deformable Template Matching Method for Automatic Rib Centerline Extraction and Labeling in CT Images, IEEE, 980-987 (2012).

FIG. 1A  FIG. 1B

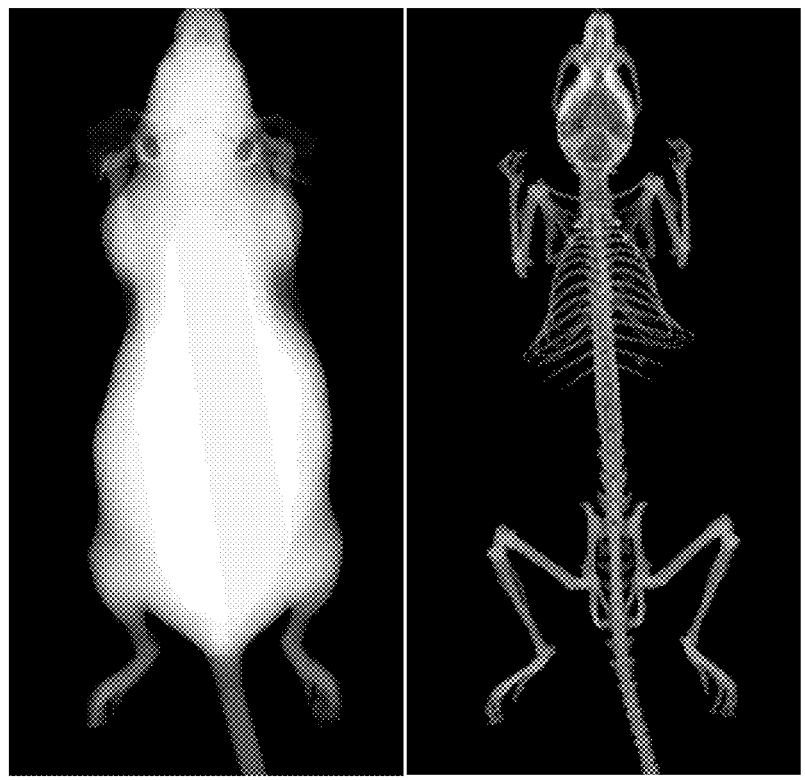
FIG. 6A
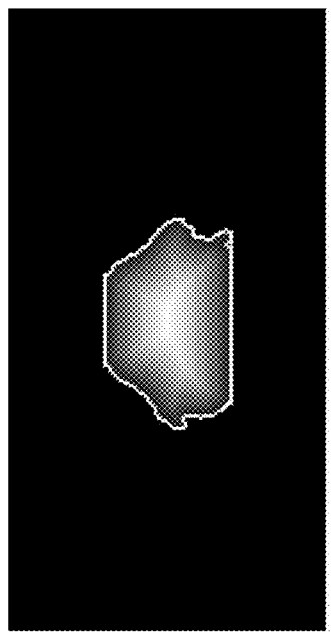 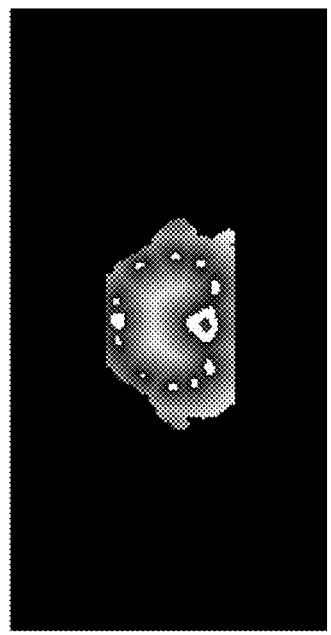
FIG. 6B          FIG. 6C

METHOD AND SYSTEM FOR AUTOMATED DETECTION OF TISSUE INTERIOR TO A MAMMALIAN RIBCAGE FROM AN IN VIVO IMAGE

TECHNICAL FIELD

This invention relates generally to methods and systems of image analysis. More particularly, in certain embodiments, the invention relates to the automated detection of tissue interior to a mammalian rib cage.

BACKGROUND

There are a wide array of technologies directed to in vivo imaging of mammals—for example, bioluminescence, fluorescence, tomography, and multimodal imaging technologies. In vivo imaging of small mammals is performed by a large community of investigators in various fields, e.g., oncology, infectious disease, and drug discovery.

In vivo imaging often involves the use of reagents, such as fluorescent probes, for non-invasive spatiotemporal visualization of biological phenomena inside a live animal. For example, fluorescence molecular tomography (FMT) involves in vivo imaging of mammals for quantitative analysis of administered and/or endogenous probes. In vivo microCT imaging, is an x-ray-based technology that can image tissues, organs, and non-organic structures with an extremely high resolution. MicroCT has evolved quickly, requiring low dose scanning and fast imaging protocols to facilitate multi-modal applications and enable longitudinal experimental models. Multi-modal imaging involves the fusion of images obtained in different ways, for example, by combining FMT, PET, MRI, CT, and/or SPECT imaging data.

Acquisition of such in vivo images can be time consuming, and rapid analysis of the acquired images is key to the efficiency of the process. Often, it is desirable to focus imaging efforts on only those portions of the mammal interior to the rib cage, which contains many organs of interest and for which advanced image analysis is needed. Advanced image analysis may involve, for example, advanced tomographic reconstruction for the quantitative analysis of an administered or endogenous probe in one or more target organs of the mammal. The portions of an image outside those target organs may not be important to the analysis, and processing time spent on those portions is wasted and results in reduced efficiency.

There is a need for a highly efficient method for detecting regions of interest of an in vivo mammalian image in order to eliminate unnecessary processing of unimportant regions of the image and reduce overall image processing time without losing important image detail.

SUMMARY OF THE INVENTION

Described herein are systems and methods for efficient and accurate automated detection of a region of interest from an in vivo mammalian image. An important region of an imaged mammal is the tissue interior to the ribcage, where key organs lie. By automatically identifying this important region, further analysis and/or processing of the image can be performed on this region without unnecessarily wasting time processing other regions of the image.

An automated procedure for identifying this region is not a simple problem, since the procedure must accurately identify the desired region for a wide range of sizes and shapes of the animals being imaged (must account for variability of the individual animals being imaged), and must be a highly computationally efficient procedure.

It is found that efficient, automated identification of the region of interest interior to the ribcage can be achieved by the use of both a bone distance mask and a surface distance mask. The technique solves the problem of accurate and fast identification of the region of interest for a wide range of sizes and shapes of mammals, e.g., small mammals such as mice.

In one aspect, the invention is directed to a method for automatically detecting (e.g., graphically isolating) a region of interest in a 3D image of a mammal corresponding to (e.g., limited to) soft tissue largely or exclusively interior to the mammal rib cage, the method comprising: automatically determining from the 3D image of the mammal, by a processor of a computing device, a surface distance image comprising intensity values at each of a plurality of points in three dimensions, each of the intensity values corresponding to a distance from a given point in 3D space to the nearest point on the outer surface of the mammal; automatically determining, by the processor, a bone distance image comprising intensity values at each of a plurality of points in three dimensions, each of the intensity values corresponding to a distance from a given point in 3D space to the nearest identified bone tissue of the mammal; and automatically detecting, by the processor, the region of interest corresponding to soft tissue interior to the mammal rib cage using the surface distance image and the bone distance image.

In some embodiments, the detecting step comprises: applying, by the processor, a threshold to the surface distance image to determine a surface distance mask corresponding to a central region of the mammal body (e.g., wherein the surface distance mask identifies one or more discrete volumes within the mammal body); applying, by the processor, a threshold to the bone distance image to determine a bone distance mask corresponding to one or more regions at least a given distance from identified bone tissue of the mammal (e.g., wherein the bone distance mask identifies one or more discrete volumes within the mammal body); applying, by the processor, an AND operation of the surface distance mask and the bone distance mask to identify only a region interior to the rib cage, within the region of interest (e.g., wherein the region identified as a result of the AND operation defines one or more discrete volumes within the mammal body) (and, optionally, applying a filter, e.g., a volume threshold, to the result of the AND operation to remove one or more volumes that lie outside the ribcage); and applying, by the processor, a dilation operation and/or a watershed operation to expand outward a region identified following the AND operation outward (e.g., and following any subsequent filtering step) that is interior to the ribcage, without encroaching the identified bone tissue, thereby detecting the region of interest interior to the mammal rib cage. For example, there may be one discrete volume identified as a result of the AND operation, where the one discrete volume is located interior to the ribcage, and dilation In some embodiments, the method further comprises determining, by the processor, a transverse plane corresponding to a lower end of the rib cage. In some embodiments, determining the transverse plane comprises estimating a transverse coordinate corresponding to the lower end of the rib cage from the surface distance image and the bone distance image.

In some embodiments, the detecting step comprises: automatically determining, by the processor, a search region mask from values of distance from front (abdominal) surface to nearest bone expressed as a function of nose-to-tail z-coordinate, said search region mask identifying a volume of the mammal excluding regions of the head above the neck and excluding regions below the rib cage; automatically determining, by the processor, a bone distance mask using the bone distance image (e.g., by applying a threshold to the bone distance image), wherein the bone distance mask corresponds to one or more regions at least a given distance from identified bone tissue of the mammal; automatically determining, by the processor, a surface distance mask using the surface distance image (e.g., by applying a threshold to the surface distance image) corresponding to one or more regions at least a given distance from the outer surface of the mammal; applying, by the processor, an AND operation of the search region mask, the bone distance mask, and the surface distance mask, then, optionally, applying a filter to the result of the AND operation to remove small distinct regions smaller than a determined threshold volume, thereby identifying seed a region interior to the rib cage, within the region of interest; and applying, by the processor, a dilation operation and/or a watershed operation to expand the seed region identified following the AND operation outward, without encroaching the identified bone tissue, then applying, by the processor, an AND operation of the result of the dilation and/or watershed operation with the search region mask, thereby detecting the region of interest interior to the mammal rib cage.

In some embodiments, the detecting step comprises: automatically determining, by the processor, a search region mask using values of distance from front (abdominal) surface to nearest bone expressed as a function of nose-to-tail z-coordinate, said search region mask identifying a volume of the mammal excluding regions of the head above the neck and excluding regions below the rib cage; automatically determining, by the processor, a bone distance mask using the bone distance image, wherein the bone distance mask corresponds to one or more regions at least a given distance from identified bone tissue of the mammal; automatically determining, by the processor, a composite distance image computed as the difference between the surface distance image and the bone distance image (e.g., wherein intensity values of the composite distance image reflect the difference between distance from bones and distance from outer surface of the mammal); applying, by the processor, a threshold to the composite distance image to determine a composite distance mask; applying, by the processor, an AND operation of the search region mask, the bone distance mask, and the composite distance mask, then, optionally, applying a filter to the result of the AND operation to remove small distinct regions smaller than a determined threshold volume, thereby identifying a seed region interior to the rib cage, within the region of interest; and applying, by the processor, a dilation operation and/or a watershed operation to expand the seed region identified following the AND operation outward, without encroaching the identified bone tissue, then applying, by the processor, an AND operation of the result of the dilation and/or watershed operation with the search region mask, thereby detecting the region of interest interior to the mammal rib cage.

In some embodiments, the detecting step comprises: automatically determining, by the processor, a bone distance mask using the bone distance image, wherein the bone distance mask corresponds to one or more regions at least a given distance from identified bone tissue of the mammal; automatically determining, by the processor, a composite distance image computed as the difference between the surface distance image and the bone distance image (e.g., wherein intensity values of the composite distance image reflect the difference between distance from bones and distance from outer surface of the mammal); applying, by the processor, a threshold to the composite distance image to determine a composite distance mask; applying, by the processor, an AND operation of the bone distance mask and the composite distance mask, then, optionally, applying a filter to the result of the AND operation to remove small distinct regions smaller than a determined threshold volume, thereby identifying an intermediate result; and automatically determining, by the processor, using the composite distance mask, a transverse plane corresponding to a lower end of the rib cage (e.g., identifying a z-coordinate along the length of the mammal where cross-section of the composite distance mask has maximal area), and removing from the intermediate result all volumes below said transverse plane, thereby identifying a seed region interior to the rib cage, within the region of interest, then applying, by the processor, a dilation operation and/or a watershed operation to expand the resulting seed region outward, without encroaching the identified bone tissue, then, optionally, filtering all volumes below said determined transverse plane, thereby detecting the region of interest interior to the mammal rib cage.

In another aspect, the invention is directed to a method for automatically detecting (e.g., graphically isolating) a region of interest in a 3D image of a mammal corresponding to (e.g., limited to) soft tissue largely or exclusively interior to the mammal rib cage, the method comprising:

at least one of (a) and (b), as follows:

(a) automatically determining using the 3D image of the mammal, by the processor, a surface distance image comprising intensity values at each of a plurality of points in three dimensions, each of the intensity values corresponding to a distance from a given point in 3D space to the nearest point on the outer surface of the mammal, and applying, by the processor, a threshold to the surface distance image to determine a surface distance mask corresponding to a central region of the mammal body (e.g., wherein the surface distance mask identifies one or more discrete volumes within the mammal body);

(b) automatically determining using the 3D image of the mammal, by a processor of a computing device, a body mask corresponding to mammal body, and applying an erosion operation to the body mask (e.g., using a disk kernel of radius R') to obtain a surface distance mask equivalent;

and at least one of (c) and (d), as follows:

(c) automatically determining using the 3D image of the mammal, by the processor, a bone distance image comprising intensity values at each of a plurality of points in three dimensions, each of the intensity values corresponding to a distance from a given point in 3D space to the nearest identified bone tissue of the mammal, and applying, by the processor, a threshold to the bone distance image to determine a bone distance mask corresponding to one or more regions at least a given distance from identified bone tissue of the mammal (e.g., wherein the bone distance mask identifies one or more volumes within the mammal body);

(d) automatically determining using the 3D image of the mammal, by the processor, a bone mask corresponding to bone tissue, and applying a dilation operation to the bone mask (e.g., using a disk kernel of radius R) (e.g., and invert) to obtain a bone distance mask equivalent;

and automatically detecting, by the processor, the region of interest corresponding to soft tissue interior to the mammal rib cage using (i) at least one of the surface distance mask and the surface distance mask equivalent, and (ii) at least one of the bone distance mask and the bone distance mask equivalent.

In some embodiments, the method further comprises determining, by the processor, a transverse plane corresponding to a lower end of the rib cage. In some embodiments, determining the transverse plane comprises estimating a transverse coordinate corresponding to the lower end of the rib cage from the surface distance image and the bone distance image.

In some embodiments, the detecting step comprises: automatically determining, by the processor, a search region mask from values of distance from front (abdominal) surface to nearest bone expressed as a function of nose-to-tail z-coordinate, said search region mask identifying a volume of the mammal excluding regions of the head above the neck and excluding regions below the rib cage; applying, by the processor, an AND operation of the search region mask, the bone distance mask (or bone distance mask equivalent), and the surface distance mask (or surface distance mask equivalent), then, optionally, applying a filter to the result of the AND operation to remove small distinct regions smaller than a determined threshold volume, thereby identifying a seed region interior to the rib cage, within the region of interest; and applying, by the processor, a dilation operation and/or a watershed operation to expand the seed region identified following the AND operation outward, without encroaching the identified bone tissue, then applying, by the processor, an AND operation of the result of the dilation and/or watershed operation with the search region mask, thereby detecting the region of interest interior to the mammal rib cage.

In some embodiments, the detecting step comprises: automatically determining, by the processor, a search region mask using values of distance from front (abdominal) surface to nearest bone expressed as a function of nose-to-tail z-coordinate, said search region mask identifying a volume of the mammal excluding regions of the head above the neck and excluding regions below the rib cage; automatically determining, by the processor, a composite distance image computed as the difference between the surface distance image and the bone distance image (e.g., wherein intensity values of the composite distance image reflect the difference between distance from bones and distance from outer surface of the mammal); applying, by the processor, a threshold to the composite distance image to determine a composite distance mask; applying, by the processor, an AND operation of the search region mask, the bone distance mask, and the composite distance mask, then, optionally, applying a filter to the result of the AND operation to remove small distinct regions smaller than a determined threshold volume, thereby identifying a seed region interior to the rib cage, within the region of interest; and applying, by the processor, a dilation operation and/or a watershed operation to expand the seed region identified following the AND operation outward, without encroaching the identified bone tissue, then applying, by the processor, an AND operation of the result of the dilation and/or watershed operation with the search region mask, thereby detecting the region of interest interior to the mammal rib cage.

In some embodiments, detecting step comprises: automatically determining, by the processor, a composite distance image computed as the difference between the surface distance image and the bone distance image (e.g., wherein intensity values of the composite distance image reflect the difference between distance from bones and distance from outer surface of the mammal); applying, by the processor, a threshold to the composite distance image to determine a composite distance mask; applying, by the processor, an AND operation of the bone distance mask and the composite distance mask, then, optionally, applying a filter to the result of the AND operation to remove small distinct regions smaller than a determined threshold volume, thereby identifying an intermediate result; and automatically determining, by the processor, using the composite distance mask, a transverse plane corresponding to a lower end of the rib cage (e.g., identifying a z-coordinate along the length of the mammal where cross-section of the composite distance mask has maximal area), and removing from the intermediate result all volumes below said transverse plane, thereby identifying a seed region interior to the rib cage, within the region of interest, then applying, by the processor, a dilation operation and/or a watershed operation to expand the resulting seed region outward, without encroaching the identified bone tissue, then, optionally, filtering all volumes below said determined transverse plane, thereby detecting the region of interest interior to the mammal rib cage.

In another aspect, the invention is directed to a system comprising: a processor; and a memory having instructions stored thereon, wherein the instructions, when executed by the processor, cause the processor to:
(i) at least one of (a) and (b), as follows:
  (a) automatically determine, using the 3D image of the mammal, a surface distance image comprising intensity values at each of a plurality of points in three dimensions, each of the intensity values corresponding to a distance from a given point in 3D space to the nearest point on the outer surface of the mammal, and apply a threshold to the surface distance image to determine a surface distance mask corresponding to a central region of the mammal body (e.g., wherein the surface distance mask identifies one or more discrete volumes within the mammal body);
  (b) automatically determine, using the 3D image of the mammal, a body mask corresponding to mammal body, and apply an erosion operation to the body mask (e.g., using a disk kernel of radius R') to obtain a surface distance mask equivalent; and
(ii) at least one of (c) and (d), as follows:
  (c) automatically determine, using the 3D image of the mammal, a bone distance image comprising intensity values at each of a plurality of points in three dimensions, each of the intensity values corresponding to a distance from a given point in 3D space to the nearest identified bone tissue of the mammal, and apply a threshold to the bone distance image to determine a bone distance mask corresponding to one or more regions at least a given distance from identified bone tissue of the mammal (e.g., wherein the bone distance mask identifies one or more volumes within the mammal body);
  (d) automatically determine, using the 3D image of the mammal, a bone mask corresponding to bone tissue, and apply a dilation operation to the bone mask (e.g., using a disk kernel of radius R) (e.g., and invert) to obtain a bone distance mask equivalent;
and
(iii) automatically detect, by the processor, the region of interest corresponding to soft tissue interior to the mammal rib cage using (i) at least one of the surface distance image and the surface distance image equivalent, and (ii) at least one of the bone distance image and the bone distance image equivalent.

In another aspect, the invention is directed to a non-transitory computer readable medium having instructions stored thereon, wherein the instructions, when executed by a processor, cause the processor to:
(i) at least one of (a) and (b), as follows:
  (a) automatically determine, using the 3D image of the mammal, a surface distance image comprising intensity values at each of a plurality of points in three dimensions, each of the intensity values corresponding to a distance from a given point in 3D space to the nearest point on the outer surface of the mammal, and apply a threshold to the surface distance image to determine a surface distance mask corresponding to a central region of the mammal body (e.g., wherein the surface distance mask identifies one or more discrete volumes within the mammal body);

(b) automatically determine, using the 3D image of the mammal, a body mask corresponding to mammal body, and apply an erosion operation to the body mask (e.g., using a disk kernel of radius R') to obtain a surface distance mask equivalent;

and (ii) at least one of (c) and (d), as follows:

(c) automatically determine, using the 3D image of the mammal, a bone distance image comprising intensity values at each of a plurality of points in three dimensions, each of the intensity values corresponding to a distance from a given point in 3D space to the nearest identified bone tissue of the mammal, and apply a threshold to the bone distance image to determine a bone distance mask corresponding to one or more regions at least a given distance from identified bone tissue of the mammal (e.g., wherein the bone distance mask identifies one or more volumes within the mammal body);

(d) automatically determine, using the 3D image of the mammal, a bone mask corresponding to bone tissue, and apply a dilation operation to the bone mask (e.g., using a disk kernel of radius R) (e.g., and invert) to obtain a bone distance mask equivalent; and (iii) automatically detect, by the processor, the region of interest corresponding to soft tissue interior to the mammal rib cage using (i) at least one of the surface distance image and the surface distance image equivalent, and (ii) at least one of the bone distance image and the bone distance image equivalent.

BRIEF DESCRIPTION OF THE DRAWINGS

The foregoing and other objects, aspects, features, and advantages of the invention will become more apparent and may be better understood by referring to the following description taken in conjunction with the accompanying drawings, in which:

FIGS. 1A-1I are images illustrating steps of the method of Example i for the automated detection of a region of interest interior to a mammalian ribcage from an in vivo image, according to an illustrative embodiment of the invention;

FIGS. 6A-6G are images illustrating steps of a method for automated detection of a region of interest interior to a mammalian ribcage from an in vivo image, according to an illustrative embodiment of the invention, showing transverse cross sections rather than coronal cross sections;

DETAILED DESCRIPTION

Figure 1C:
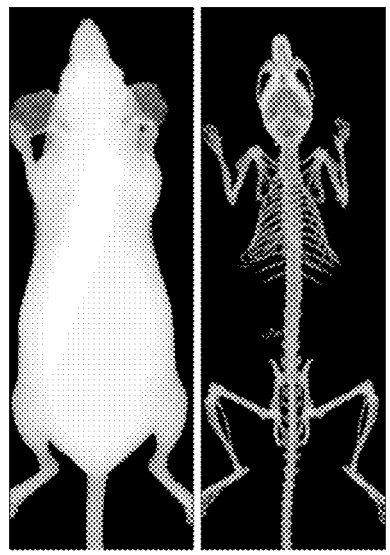
Figure 1C:
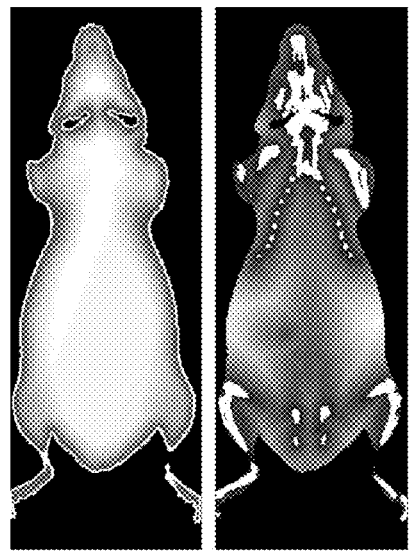
Figure 1C:
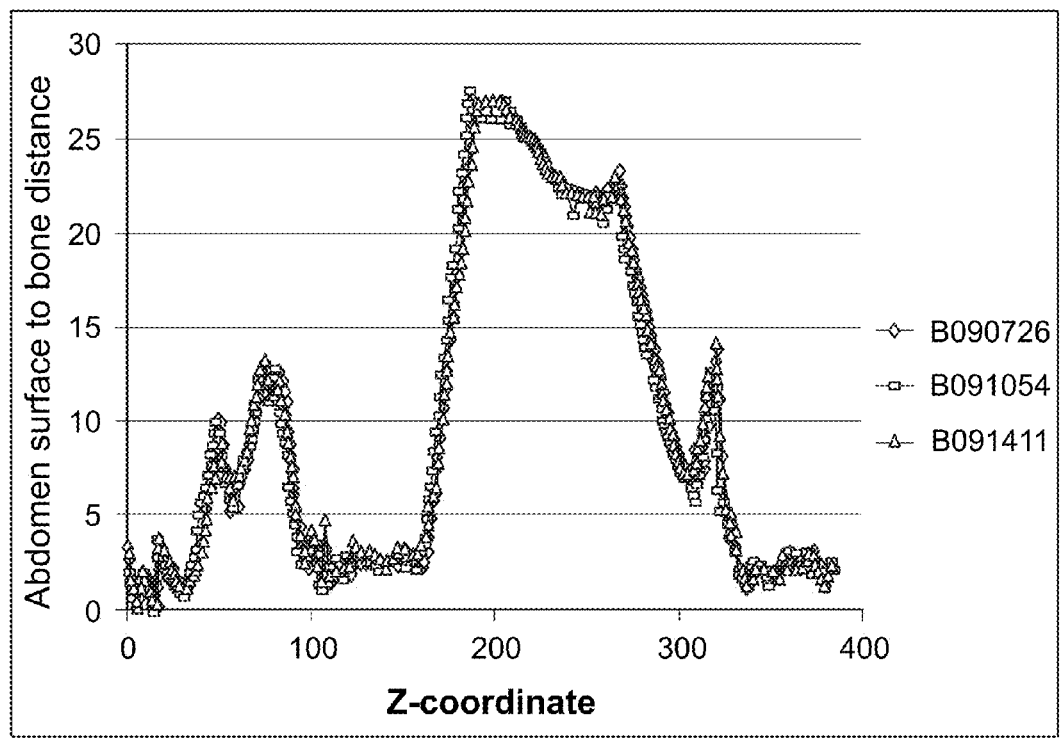

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

As used herein, an "image"—for example, a 3D image of mammal—includes any visual representation, such as a photo, a video frame, streaming video, as well as any electronic, digital or mathematical analogue of a photo, video frame, or streaming video. Any apparatus described herein, in certain embodiments, includes a display for displaying an image or any other result produced by the processor. Any method described herein, in certain embodiments, includes a step of displaying an image or any other result produced via the method.

As used herein, "3D" or "three-dimensional" with reference to an "image" means conveying information about three dimensions. A 3D image may be rendered as a dataset in three dimensions and/or may be displayed as a set of two-dimensional representations, or as a three-dimensional representation.

As used herein, a "mask" is a graphical pattern that identifies a 2D or 3D region and is used to control the elimination or retention of portions of an image or other graphical pattern.

As used herein, a "seed region" is an identified region of an image or mask which is used to calculate another, larger region, e.g., by using a dilation and/or watershed operation. Example seed regions are shown, for example, in FIG. 1H, FIG. 2H, and FIG. 3G.

Described herein are systems and methods for automated detection of a region of interest interior to a mammalian ribcage from an in vivo 3D image. The 3D image may be single image or a set of multiple images.

FIGS. 1, 2, and 3 show three different approaches, denoted as Examples i, ii, and iii, respectively. As shown herein, where a 2D coronal, transverse, or sagittal projection or cross-section is illustrated, it is to be understood there is a corresponding 3D image or 3D mask that is determined or identified. For the sake of simplicity, the 2D projection or cross-section is shown.

FIGS. 1A-1I illustrate steps in the method of Example i.

FIG. 1A shows coronal projections of a mouse body (surface) mask and a mouse bone mask, identified using an in vivo 3D image of the mouse.

FIG. 1B shows a coronal cross section of a distance image from the mouse surface (left) and a distance image from mouse bones (right), determined from the mouse body (surface) mask and the mouse bone mask. The distance images have intensities (values) that vary as a function of distance from the nearest point on the mouse surface (left) and from the nearest point corresponding to mouse bone (right), respectively. At left, the mouse surface is indicated in red, and at right, the bones are indicated in red.

Figure 1D:
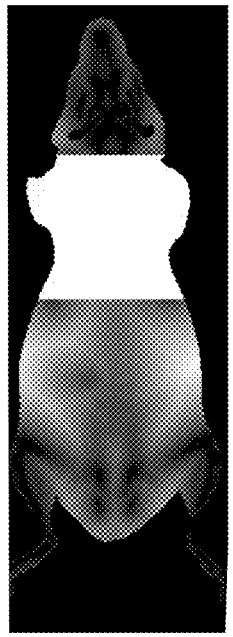

FIGS. 1C and 1D illustrate determination of a search region to narrow down the area of interest, i.e., the region of the mammal interior to the ribcage. The search region is defined by an interval of the transverse (z-, nose-to-tail) coordinate that excludes regions of the head above the neck and regions below the ribcage. FIG. 1C is a graph whose y-axis corresponds to the distance from the front (abdominal) surface of the mouse to the nearest bone, and the x-axis corresponds to the transverse (z-, nose-to-tail) coordinate, where 0 is near the tip of the nose, and the highest z-value is on the tail. The position of the neck is identified from the spike in y-values at z-coordinate of about 80 in this example, and the plane corresponding to the base of the ribcage is identified by the spike in y-values at z-coordinate of about 170 in this example, corresponding to the lower edge of the rib cage. FIG. 1C shows y-values for three different mice images, as a function of z-coordinate. It can be seen that the pattern of y-values is very similar for all three datasets. It has been found this is a very accurate, fast method for identifying the search region. FIG. 1D shows the search region identified from the graph of FIG. 1C.

Figure 1E:
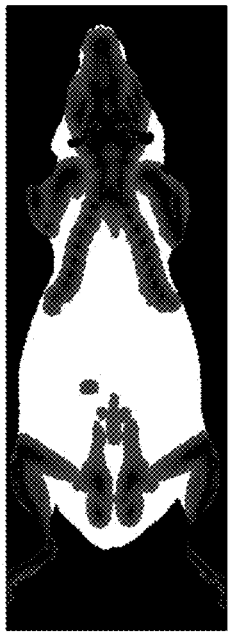

FIG. 1E is a coronal cross-section of a 3D mask following application of a threshold to the distance image from mouse bones. Here, it is desired to identify a central region of the ribcage. As can be seen from FIG. 1E, in addition to the central region of the ribcage, the result of the thresholding also includes undesired regions outside the ribcage which are far from bones.

Figure 1F:
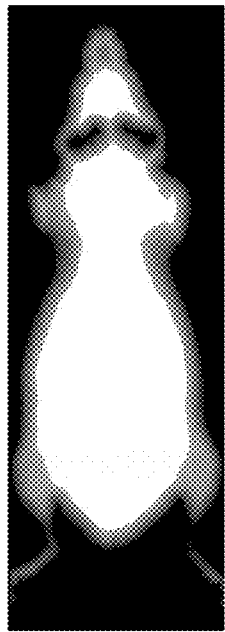

The purpose of the step illustrated by FIG. 1F is to exclude unwanted regions that are far from bones but are close to the mouse surface. Here, a threshold is applied to the distance image from the mouse surface (typically, larger than the threshold applied to the distance image from mouse bones), the result of which is shown in FIG. 1F (coronal cross-section of the resulting 3D mask).

Figure 1G:
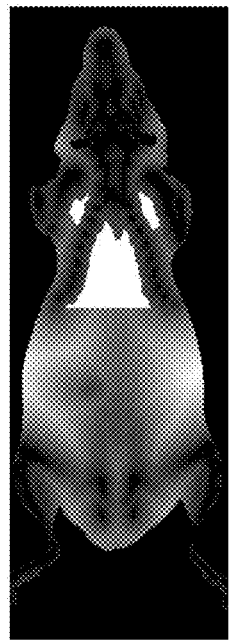
Figure 1H:
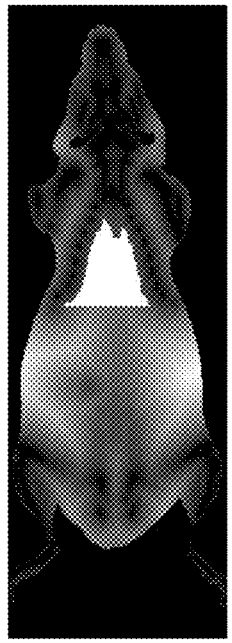

Next, an AND-operation is performed among the masks of FIGS. 1D, 1E, and 1F, which results in the mask shown in FIG. 1G. Sometimes, this yields a central region of the rib cage without any unwanted regions. However, the operation may include some unwanted regions, e.g., the two upper regions outside the ribcage in FIG. 1G. These regions may be removed on the basis of their volume—the unwanted regions are found to be smaller in size than the region of interest, and they are removed on the basis of a threshold volume. FIG. 1H shows the mask of FIG. 1G after removal of the unwanted regions on the basis of their volume, the result being an identified region entirely within the interior of the ribcage.

Figure 1I:
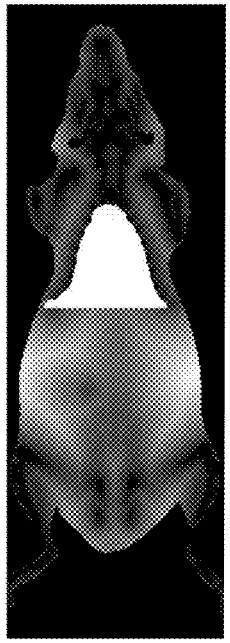

Finally, a dilation operation is applied to the mask of FIG. 1H, followed by an AND-operation with the search mask of FIG. 1D to expand the identified central region out to the ribcage bone, without extending below or above the ribcage. The result of this step is shown in FIG. 1I. Alternatively, the dilation operation can be replaced by a watershed operation, which may be slower, but is more accurate.

FIGS. 2A-2I illustrate steps in the method of Example ii.

Figures 2A, 2B:
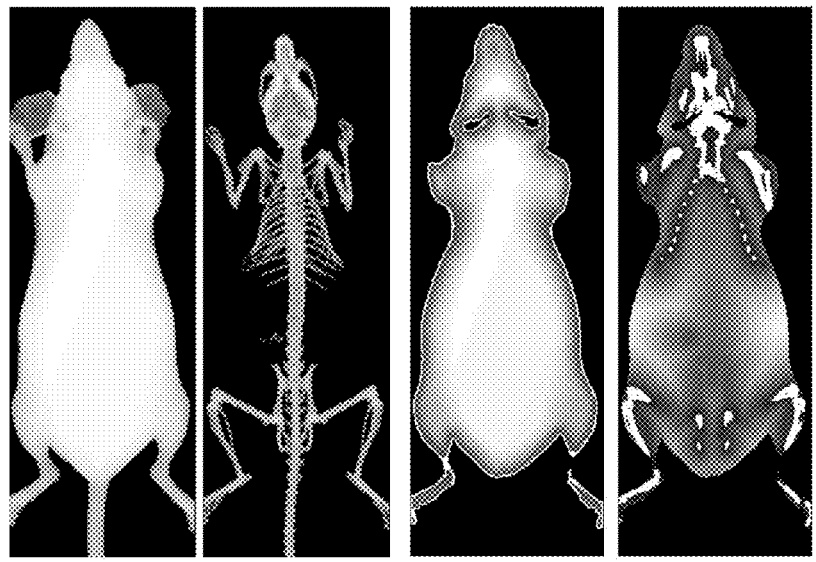
FIGS. 2A-2I are images illustrating steps of the method of Example ii for the automated detection of a region of interest interior to a mammalian ribcage from an in vivo image, according to an illustrative embodiment of the invention.

FIG. 2A shows coronal projections of a mouse body (surface) mask and a mouse bone mask, identified using an in vivo 3D image of the mouse.

FIG. 2B shows a coronal cross section of a distance image from the mouse surface (left) and a distance image from mouse bones (right), determined from the mouse body (surface) mask and the mouse bone mask. The distance images have intensities (values) that vary as a function of distance from the nearest point on the mouse surface (left) and from the nearest point corresponding to mouse bone (right), respectively. At left, the mouse surface is indicated in red, and at right, the bones are indicated in red.

Figure 2C:
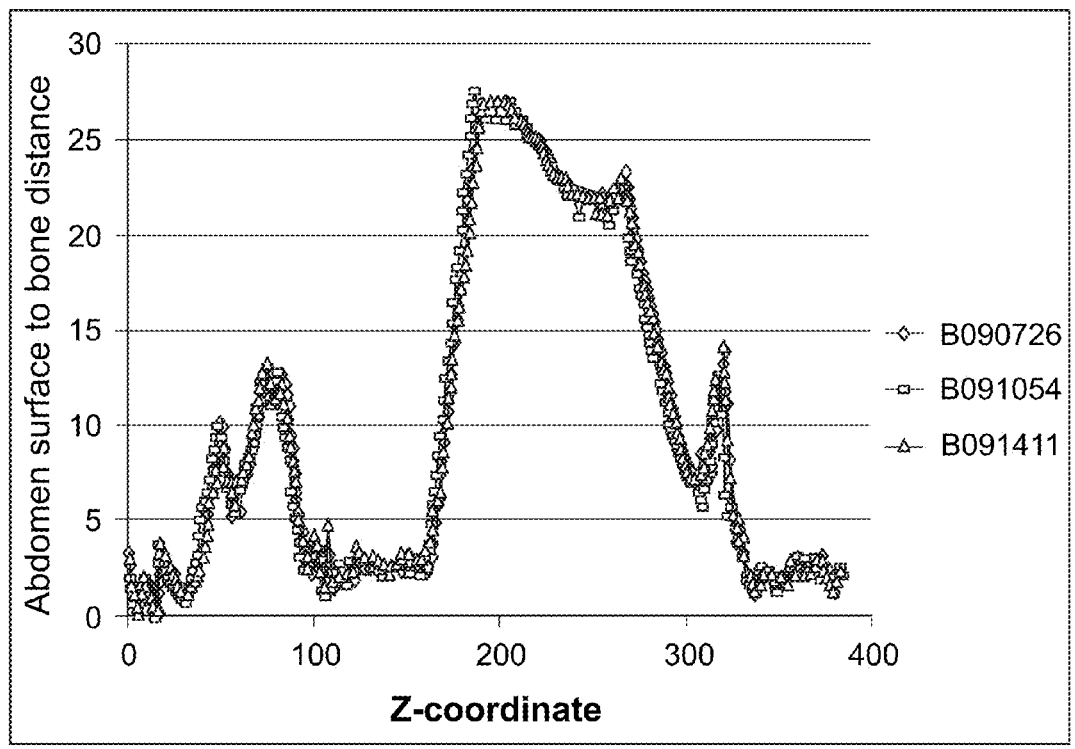
Figure 2D:
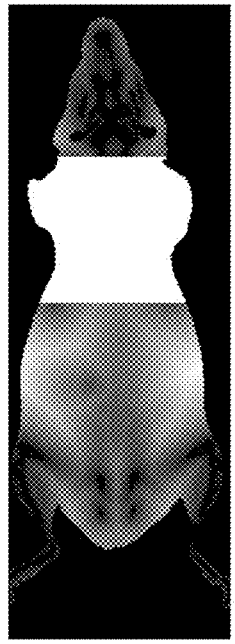

FIGS. 2C and 2D illustrate determination of a search region to narrow down the area of interest, i.e., the region of the mammal interior to the ribcage. The search region is defined by an interval of coordinate z (nose to tail) that excludes regions of the head above the neck and regions below the ribcage. FIG. 2C is a graph whose y-axis corresponds to the distance from the front (abdominal) surface of the mouse to the nearest bone, and the x-axis corresponds to the nose-to-tail z-coordinate, where 0 is the tip of the nose, and the highest z-value is the end of the tail. The position of the neck is identified from the spike in y-values at z-coordinate of about 80 in this example, and the plane corresponding to the base of the ribcage is identified by the spike in y-values at z-coordinate of about 170 in this example, corresponding to the lower edge of the rib cage. FIG. 2C shows y-values for three different mice, as a function of z-coordinate. It can be seen that the pattern of y-values is very similar for all three mice. It has been found this is a very accurate, fast method for identifying the search region. FIG. 2D shows the search region identified from the graph of FIG. 2C.

Figure 2E:
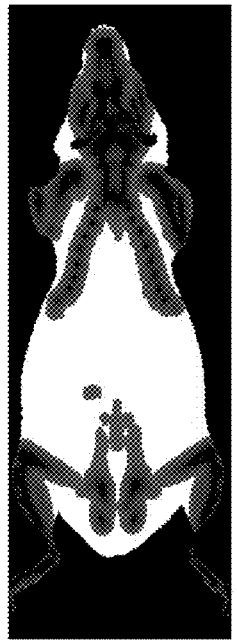

FIG. 2E is a coronal cross-section of a 3D mask following application of a threshold to the distance image from mouse bones. Here, it is desired to identify a central region of the ribcage. As can be seen from FIG. 2E, in addition to the central region of the ribcage, the result of the thresholding also includes undesired regions outside the ribcage which are far from bones.

Figure 2F:
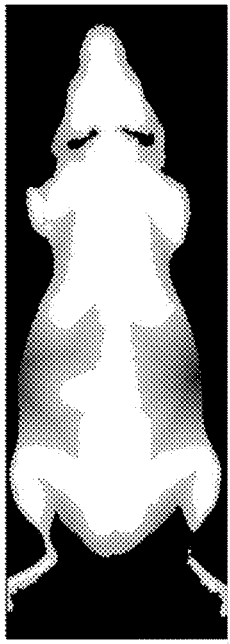

The purpose of the step illustrated by FIG. 2F is to exclude unwanted regions that are outside the ribcage. Unlike in Example i, where a threshold was applied to the distance image from the mouse surface, here in Example ii, a threshold is applied to the distance from bones minus distance from mouse surface, as determined from the two distance images (distance from mouse surface and distance from mouse bones). The resulting mask is shown in FIG. 2F.

Figure 2G:
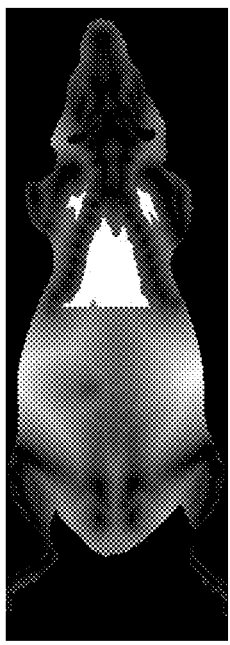
Figure 2H:
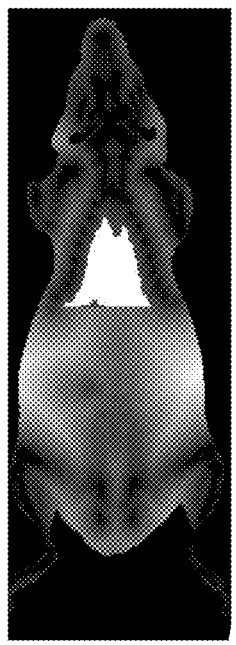

Next, an AND-operation is performed among the masks of FIGS. 2D, 2E, and 2F, which results in the mask shown in FIG. 2G. Sometimes, this yields a central region of the rib cage without any unwanted regions. However, the operation may include some unwanted regions, e.g., the two upper regions outside the ribcage in FIG. 2G. These regions may be removed on the basis of their volume—the unwanted regions are found to be smaller in size than the region of interest, and they are removed on the basis of a threshold volume. FIG. 2H shows the mask of FIG. 2G after removal of the unwanted regions on the basis of their volume, the result being an identified region entirely within the interior of the ribcage.

Figure 2I:
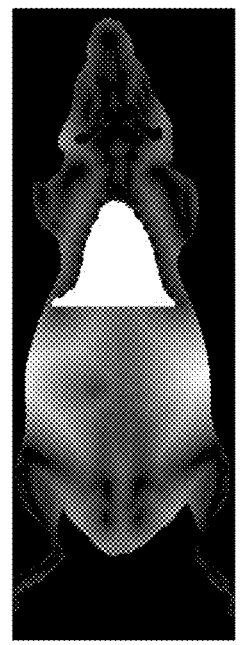

Finally, a dilation operation is applied to the mask of FIG. 2H, followed by an AND-operation with the search mask of FIG. 2D to expand the identified central region out to the ribcage bone, without extending below or above the ribcage. A simple dilation operation (without additionally using the search mask) would expand the result below the ribcage; therefore, we use a final AND-operation with the search mask. The result of this step is shown in FIG. 2I. Alternatively, the dilation operation can be replaced by a watershed operation, which may be slower, but is more accurate.

FIGS. 3A-3H illustrate steps in the method of Example iii.

Figure 3A:
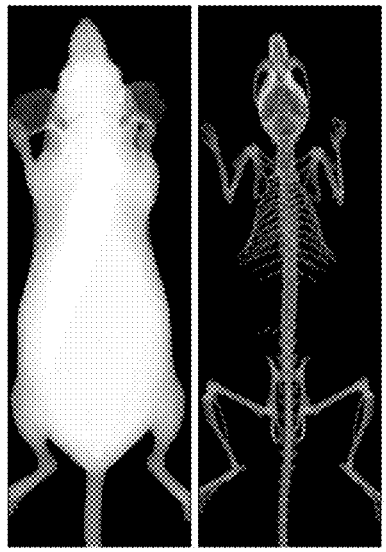
FIGS. 3A-3H are images illustrating steps of the method of Example iii for the automated detection of a region of interest interior to a mammalian ribcage from an in vivo image, according to an illustrative embodiment of the invention.

FIG. 3A shows coronal projections of a mouse body (surface) mask and a mouse bone mask, identified using an in vivo 3D image of the mouse.

Figure 3B:
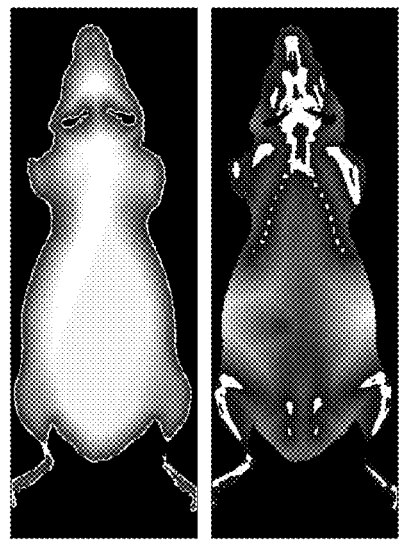

FIG. 3B shows a coronal cross section of a distance image from the mouse surface (left) and a distance image from mouse bones (right), determined from the mouse body (surface) mask and the mouse bone mask. The distance images have intensities (values) that vary as a function of distance from the nearest point on the mouse surface (left) and from the nearest point corresponding to mouse bone (right), respectively. At left, the mouse surface is indicated in red, and at right, the bones are indicated in red.

Unlike in the preceding Examples i and ii, there is no determination of a search region from a plot of abdomen-surface-to-bone-distance as a function of z-coordinate here in Example iii. Rather, in Example iii, there is a search region defined by a single transverse plane, which is estimated using a different method.

Figure 3C:

FIG. 3C is a coronal projection of a 3D mask following application of a threshold to the distance image from mouse bones. Here, it is desired to identify a central region of the ribcage. As can be seen from FIG. 3C, in addition to the central region of the ribcage, the result of the thresholding also includes undesired regions outside the ribcage which are far from bones.

A threshold is applied to the distance from bones minus distance from mouse surface, as determined from the two distance images (distance from mouse surface and distance from mouse bones). The resulting mask is shown in FIG. 3D.

Figure 3D:
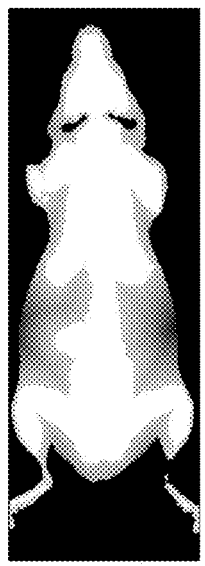
Figure 3E:

Next, an AND-operation is performed among the masks of FIGS. 3C and 3D, resulting in the mask of FIG. 3E.

Figure 3F:
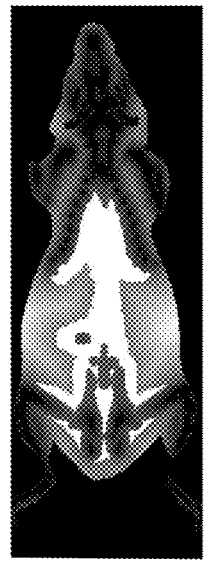

The purpose of the step illustrated by FIG. 3F is to exclude small distinct regions above the ribcage. These regions may be removed on the basis of their volume—the unwanted regions are found to be smaller in size than the main resulting region, and they are removed on the basis of a threshold volume. FIG. 3F shows the mask of FIG. 3E after removal of the unwanted regions on the basis of their volume.

This leaves an unwanted region below the ribcage. To remove the region, the z-coordinate corresponding to the base of the ribcage is determined as the coordinate where the cross-section of the mask of FIG. 3F has maximal area. The volume of the mask below this determined z-coordinate is then removed, with the resulting mask shown in FIG. 3G.

Figure 3G:
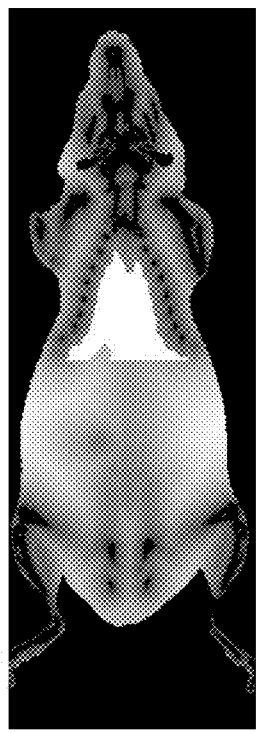
Figure 3H:
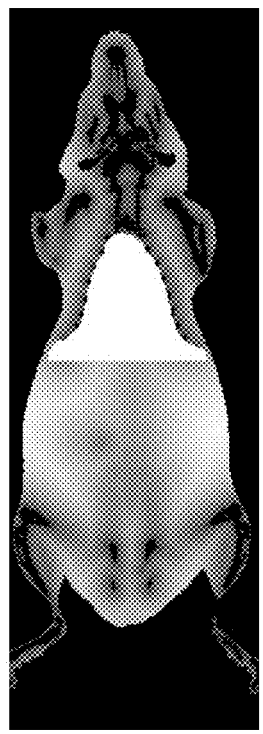

Finally, a dilation operation is applied to the mask of FIG. 3G, down to the z-coordinate identified in the previous step, thereby expanding the identified central region out to the ribcage bone, without extending below the ribcage. The result of this step is shown in FIG. 3H. Alternatively, the dilation operation can be replaced by a watershed operation, which may be slower, but is more accurate.

Figure 4A:
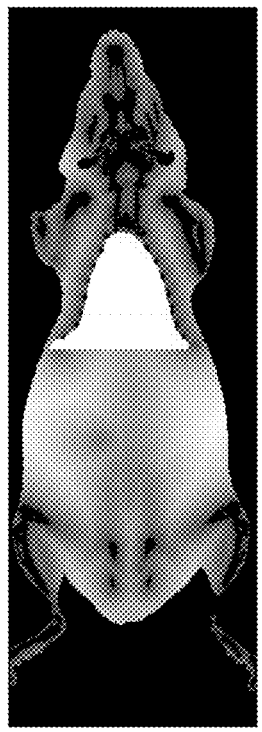
FIGS. 4A-4C are images illustrating the end results of the methods of Examples i, ii, and iii, according to illustrative embodiments of the invention.
Figure 4B:
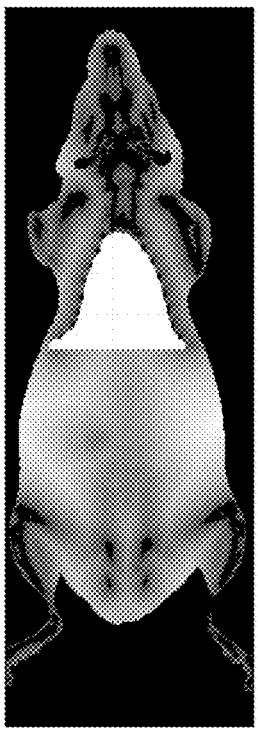
Figure 4C:
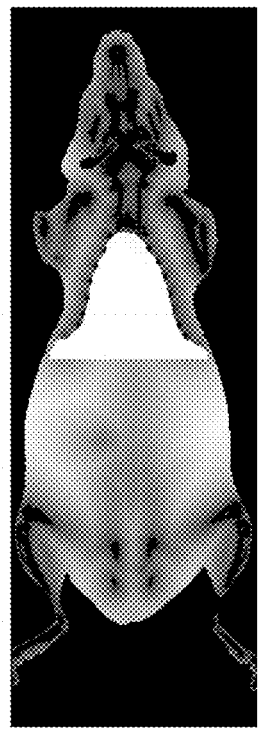

FIGS. 4A-4C are images illustrating the end results of the methods of Examples i, ii, and iii. It can be seen that the detected regions of interest using the three different approaches are nearly identical.

As illustrated in Examples i and ii, an important feature in exemplary methods for identification of the region of interest interior to the ribcage is the use of both a bone distance mask and a surface distance mask.

A bone distance mask can be determined from a bone distance image, as in the examples above, or, alternatively (and equivalently), a bone distance mask can be determined directly from the bone mask as identified from a 3D image of the mammal. Similarly, a surface distance mask can be determined from a surface distance image, as in Examples i, ii, and iii above, or, alternatively (and equivalently), a surface distance mask can be determined directly from the mammal body (surface) mask as identified from a 3D image of the mammal.

Figure 5:
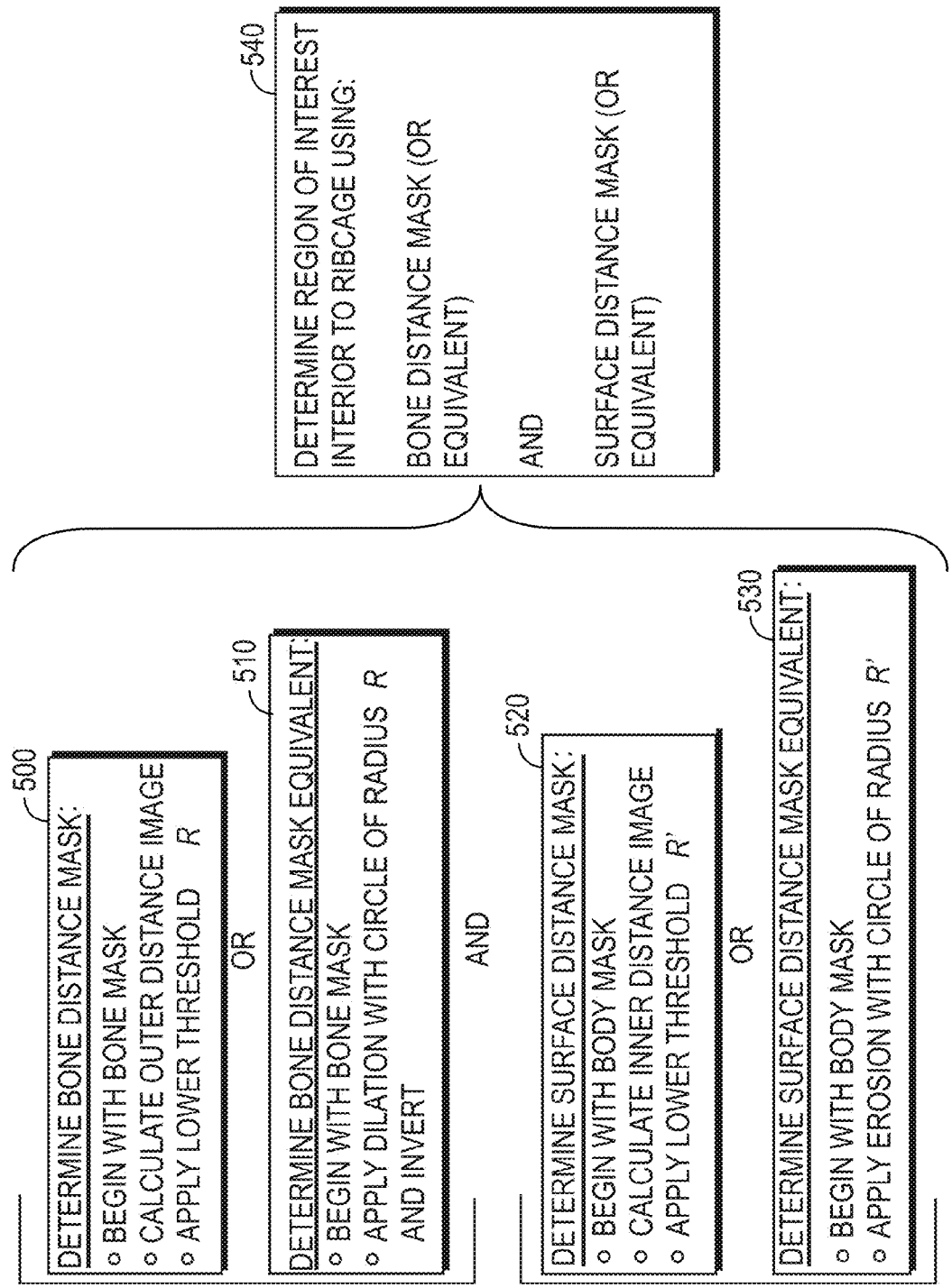
FIG. 5 is a flow chart illustrating a method for automated detection of a region of interest interior to a mammalian ribcage from an in vivo image, according to an illustrative embodiment of the invention.

Further clarifying this point, FIG. 5 is a flow chart illustrating a method for automated detection of a region of interest interior to a mammalian ribcage from an in vivo image, according to an illustrative embodiment. Either a bone distance mask is determined as in step 500—e.g., by starting with a bone mask as determined from a 3D image of the mammal, calculating an outer distance image, and applying a lower threshold R—or a bone distance mask equivalent is determined as in step 510—e.g., by starting with the bone mask and applying dilation with a disk of radius R, then inverting. Next, a surface distance mask is determined as in step 520—e.g., by beginning with a body mask as identified from a 3D image of the mammal, then calculating an inner distance image and applying a lower threshold R'—or a surface distance mask equivalent is determined as in step 530—e.g., by starting with the body (surface) mask and applying erosion with a disk of radius R'.

Then, in step 540, the bone distance mask (or bone distance mask equivalent) and the surface distance mask (or surface distance mask equivalent) is used to determine the desired region of interest interior to the ribcage.

Figure 6D:
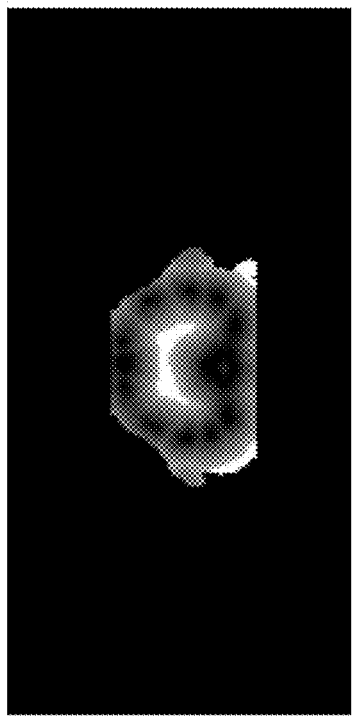

FIGS. 6A-6G are images illustrating steps of a method for automated detection of a region of interest interior to a mammalian ribcage from an in vivo image, according to an illustrative embodiment, which show transverse cross sections rather than coronal cross sections. FIG. 6A shows coronal projections of the mouse body mask and the mouse bone mask. FIG. 6B shows a transverse cross section of the distance image to mouse surface, and FIG. 6C shows a transverse cross section of the distance image to bones. The mouse surface is shown in red in FIG. 6B, and the bones are shown in red in FIG. 6C.

FIG. 6D illustrates a mask created by applying a threshold to the distance image from bones. The central region of the ribcage is detected, but there are other unwanted regions included in the mask.

Figure 6E:
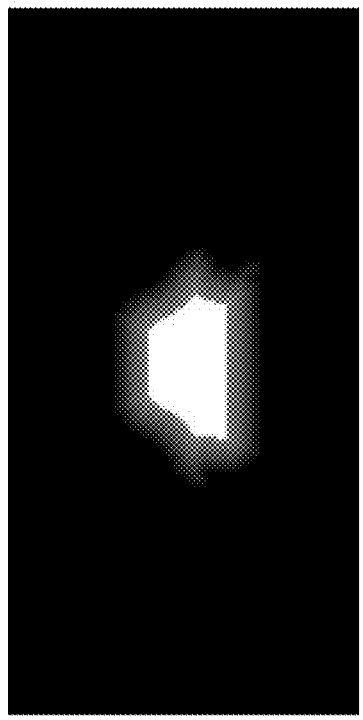
Figure 6F:
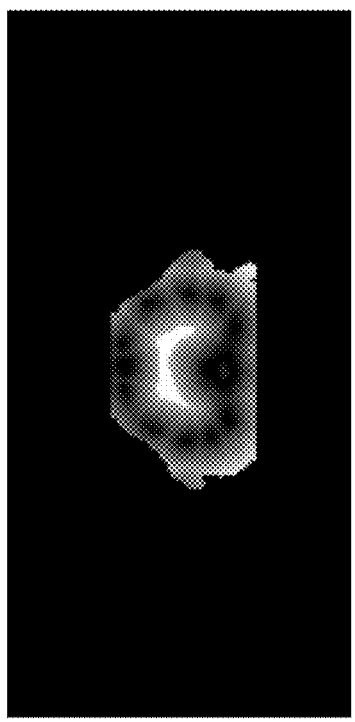
Figure 6G:
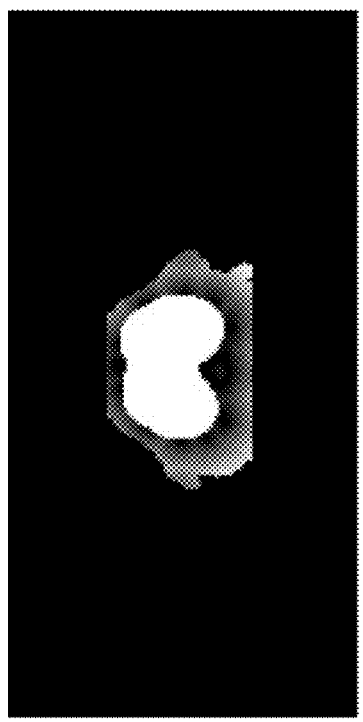

FIG. 6E illustrates a mask created by applying a threshold to the distance image from the mouse surface, which is used to eliminate the unwanted regions of the mask of FIG. 6D. FIG. 6F shows the result of an AND-operation between the masks of FIGS. 6D and 6E, eliminating the unwanted regions. FIG. 6G shows the result of dilation of the mask of FIG. 6F out to the bone surface (ribcage bone).

Figure 7A:
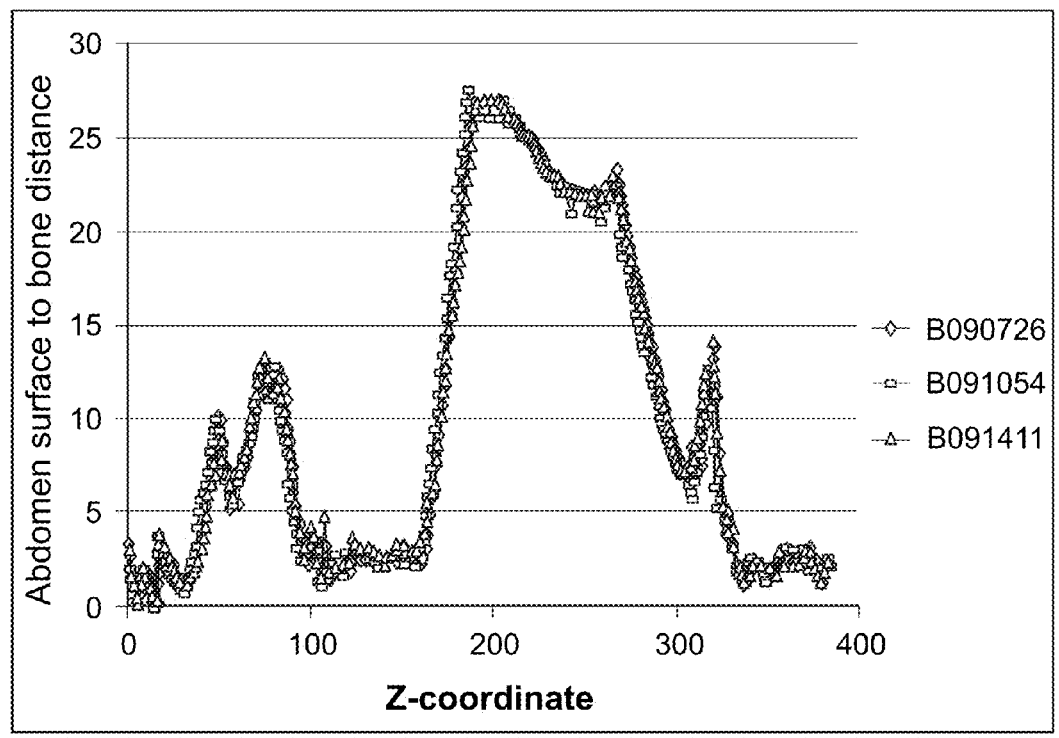
FIGS. 7A and 7B are images illustrating identification of a search region in a method for automated detection of a region of interest interior to a mammalian ribcage, according to an illustrative embodiment of the invention, showing coronal, transverse, and sagittal planes.
Figure 7B:
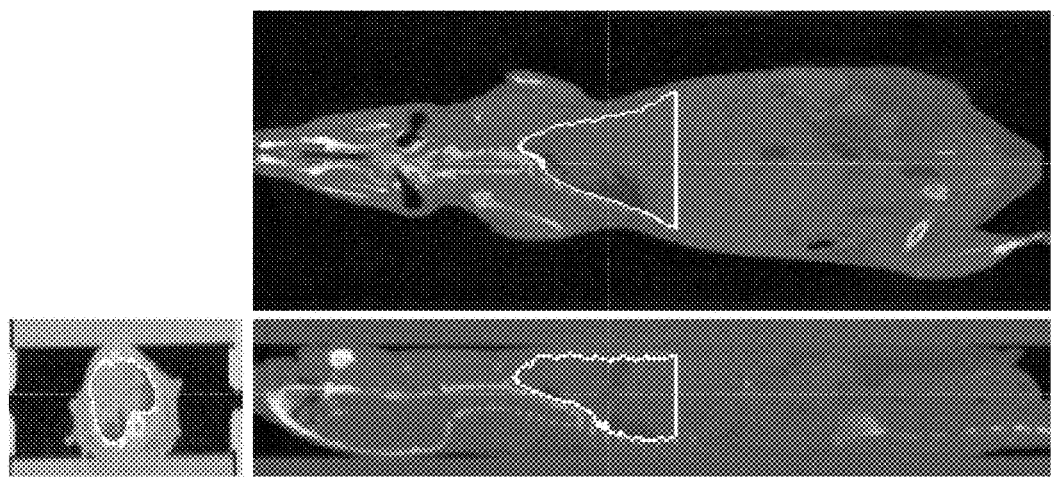

The ribcage is open from below, and regions of the resulting mask below the plane of the ribcage should be removed. FIGS. 7A and 7B illustrate identification of the transverse plane from a plot of abdomen-surface-to-bone-distance as a function of nose-to-tail z-coordinate, as described before, with the z-coordinate of about 170 corresponding to the transverse plane at the base of the ribcage.

FIG. 7B shows resulting borders of the region of interest interior to the ribcage outlined in red in coronal, transverse, and sagittal plane cross-sections, as detected via the exemplary method.

Figure 8:
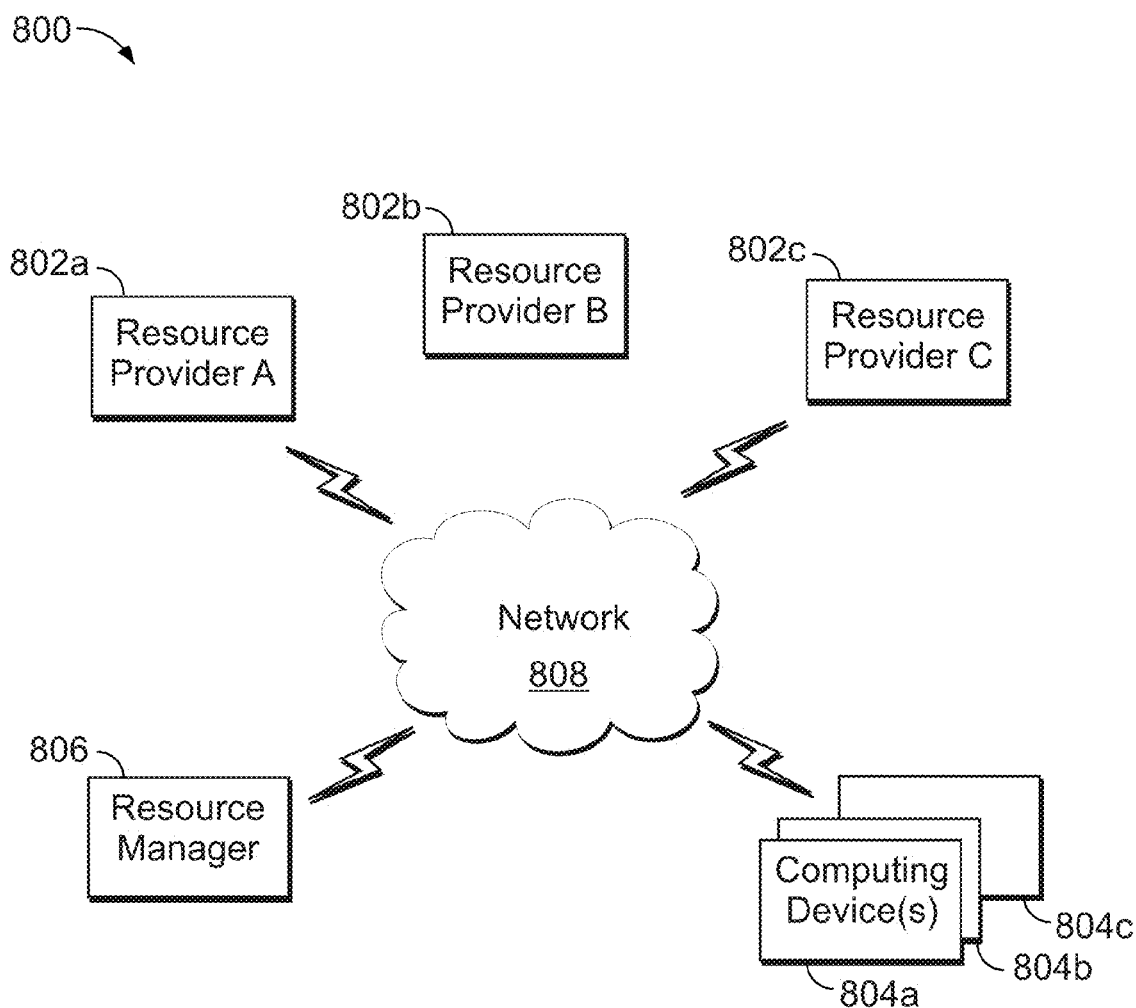
FIG. 8 is a block diagram of an example network environment for use in the methods and systems for automated detection of a region of interest interior to a mammalian ribcage from an in vivo image, according to an illustrative embodiment.

FIG. 8 shows an illustrative network environment Error! Reference source not found.00 for use in the methods and systems for automated detection of a region of interest interior to a mammalian ribcage from an in vivo image, as described herein. In brief overview, referring now to FIG. 8, a block diagram of an exemplary cloud computing environment 800 is shown and described. The cloud computing environment 800 may include one or more resource providers 802a, 802b, 802c (collectively, 802). Each resource provider 802 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 802 may be connected to any other resource provider 802 in the cloud computing environment 800. In some implementations, the resource providers 802 may be connected over a computer network 808. Each resource provider 802 may be connected to one or more computing device 804a, 804b, 804c (collectively, 804), over the computer network 808.

The cloud computing environment 800 may include a resource manager 806. The resource manager 806 may be connected to the resource providers 802 and the computing devices 804 over the computer network 808. In some implementations, the resource manager 806 may facilitate the provision of computing resources by one or more resource providers 802 to one or more computing devices 804. The resource manager 806 may receive a request for a computing resource from a particular computing device 804. The resource manager 806 may identify one or more resource providers 802 capable of providing the computing resource requested by the computing device 804. The resource manager 806 may select a resource provider 802 to provide the computing resource. The resource manager 806 may facilitate a connection between the resource provider 802 and a particular computing device 804. In some implementations, the resource manager 806 may establish a connection between a particular resource provider 802 and a particular computing device 804. In some implementations, the resource manager 806 may redirect a particular computing device 804 to a particular resource provider 802 with the requested computing resource.

Figure 9:
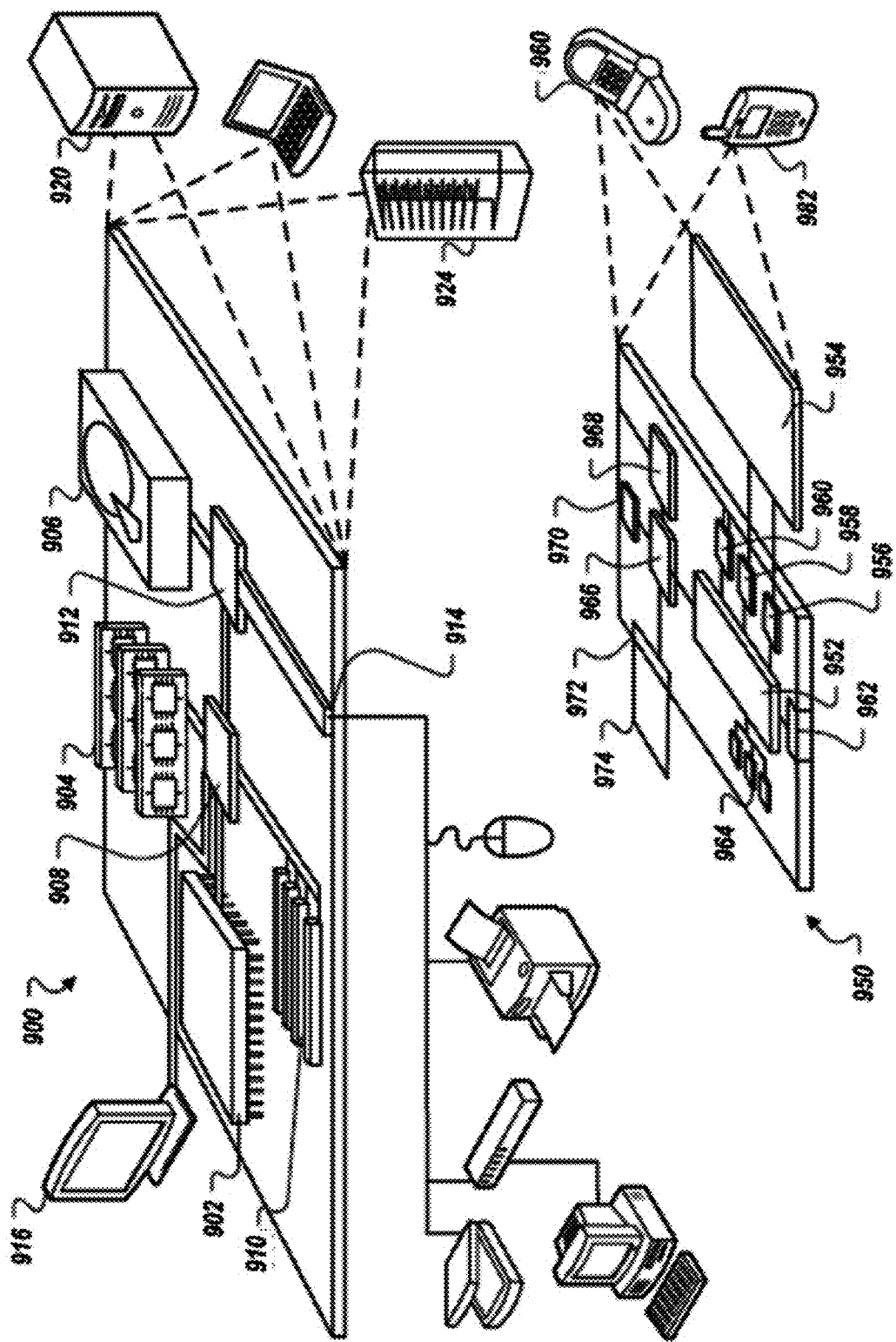
FIG. 9 is a block diagram of an example computing device and an example mobile computing device, for use in illustrative embodiments of the invention.

FIG. 9 shows an example of a computing device 900 and a mobile computing device 950 that can be used in the methods and systems described in this disclosure. The computing device 900 is intended to represent various forms of digital computers, such as laptops, desktops, workstations, personal digital assistants, servers, blade servers, mainframes, and other appropriate computers. The mobile computing device 950 is intended to represent various forms of mobile devices, such as personal digital assistants, cellular telephones, smartphones, and other similar computing devices. The components shown here, their connections and relationships, and their functions, are meant to be examples only, and are not meant to be limiting.

The computing device 900 includes a processor 902, a memory 904, a storage device 906, a high-speed interface 908 connecting to the memory 904 and multiple high-speed expansion ports 910, and a low-speed interface 912 connecting to a low-speed expansion port 914 and the storage device 906. Each of the processor 902, the memory 904, the storage device 906, the high-speed interface 908, the high-speed expansion ports 910, and the low-speed interface 912, are interconnected using various busses, and may be mounted on a common motherboard or in other manners as appropriate. The processor 902 can process instructions for execution within the computing device 900, including instructions stored in the memory 904 or on the storage device 906 to display graphical information for a GUI on an external input/output device, such as a display 916 coupled to the high-speed interface 908. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 904 stores information within the computing device 900. In some implementations, the memory 904 is a volatile memory unit or units. In some implementations, the memory 904 is a non-volatile memory unit or units. The memory 904 may also be another form of computer-readable medium, such as a magnetic or optical disk.

The storage device 906 is capable of providing mass storage for the computing device 900. In some implementations, the storage device 906 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 902), perform one or more methods, such as those described above. The instructions can also be stored by one or more storage devices such as computer- or machine-readable mediums (for example, the memory 904, the storage device 906, or memory on the processor 902).

The high-speed interface 908 manages bandwidth-intensive operations for the computing device 900, while the low-speed interface 912 manages lower bandwidth-intensive operations. Such allocation of functions is an example only. In some implementations, the high-speed interface 908 is coupled to the memory 904, the display 916 (e.g., through a graphics processor or accelerator), and to the high-speed expansion ports 910, which may accept various expansion cards (not shown). In the implementation, the low-speed interface 912 is coupled to the storage device 906 and the low-speed expansion port 914. The low-speed expansion port 914, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 900 may be implemented in a number of different forms, as shown in the figure. For example, it may be implemented as a standard server 920, or multiple times in a group of such servers. In addition, it may be implemented in a personal computer such as a laptop computer 922. It may also be implemented as part of a rack server system 924. Alternatively, components from the computing device 900 may be combined with other components in a mobile device (not shown), such as a mobile computing device 950. Each of such devices may contain one or more of the computing device 900 and the mobile computing device 950, and an entire system may be made up of multiple computing devices communicating with each other.

The mobile computing device 950 includes a processor 952, a memory 964, an input/output device such as a display 954, a communication interface 966, and a transceiver 968, among other components. The mobile computing device 950 may also be provided with a storage device, such as a microdrive or other device, to provide additional storage. Each of the processor 952, the memory 964, the display 954, the communication interface 966, and the transceiver 968, are interconnected using various buses, and several of the components may be mounted on a common motherboard or in other manners as appropriate.

The processor 952 can execute instructions within the mobile computing device 950, including instructions stored in the memory 964. The processor 952 may be implemented as a chipset of chips that include separate and multiple analog and digital processors. The processor 952 may provide, for example, for coordination of the other components of the mobile computing device 950, such as control of user interfaces, applications run by the mobile computing device 950, and wireless communication by the mobile computing device 950.

The processor 952 may communicate with a user through a control interface 958 and a display interface 956 coupled to the display 954. The display 954 may be, for example, a TFT (Thin-Film-Transistor Liquid Crystal Display) display or an OLED (Organic Light Emitting Diode) display, or other appropriate display technology. The display interface 956 may comprise appropriate circuitry for driving the display 954 to present graphical and other information to a user. The control interface 958 may receive commands from a user and convert them for submission to the processor 952. In addition, an external interface 962 may provide communication with the processor 952, so as to enable near area communication of the mobile computing device 950 with other devices. The external interface 962 may provide, for example, for wired communication in some implementations, or for wireless communication in other implementations, and multiple interfaces may also be used.

The memory 964 stores information within the mobile computing device 950. The memory 964 can be implemented as one or more of a computer-readable medium or media, a volatile memory unit or units, or a non-volatile memory unit or units. An expansion memory 974 may also be provided and connected to the mobile computing device 950 through an expansion interface 972, which may include, for example, a SIMM (Single In Line Memory Module) card interface. The expansion memory 974 may provide extra storage space for the mobile computing device 950, or may also store applications or other information for the mobile computing device 950. Specifically, the expansion memory 974 may include instructions to carry out or supplement the processes described above, and may include secure information also. Thus, for example, the expansion memory 974 may be provided as a security module for the mobile computing device 950, and may be programmed with instructions that permit secure use of the mobile computing device 950. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 952), perform one or more methods, such as those described above.

The instructions can also be stored by one or more storage devices, such as one or more computer- or machine-readable mediums (for example, the memory 964, the expansion memory 974, or memory on the processor 952). In some implementations, the instructions can be received in a propagated signal, for example, over the transceiver 968 or the external interface 962.

The mobile computing device 950 may communicate wirelessly through the communication interface 966, which may include digital signal processing circuitry where necessary. The communication interface 966 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 968 using a radio-frequency. In addition, short-range communication may occur, such as using a Bluetooth®, Wi-Fi™, or other such transceiver (not shown). In addition, a GPS (Global Positioning System) receiver module 970 may provide additional navigation- and location-related wireless data to the mobile computing device 950, which may be used as appropriate by applications running on the mobile computing device 950.

The mobile computing device 950 may also communicate audibly using an audio codec 960, which may receive spoken information from a user and convert it to usable digital information. The audio codec 960 may likewise generate audible sound for a user, such as through a speaker, e.g., in a handset of the mobile computing device 950. Such sound may include sound from voice telephone calls, may include recorded sound (e.g., voice messages, music files, etc.) and may also include sound generated by applications operating on the mobile computing device 950.

The mobile computing device 950 may be implemented in a number of different forms, as shown in the figure. For example, it may be implemented as a cellular telephone 980. It may also be implemented as part of a smart-phone 982, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal.

The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for automatically detecting a region of interest in a 3D image of a mammal corresponding to soft tissue largely or exclusively interior to the mammal rib cage, the method comprising:
   automatically determining from the 3D image of the mammal, by a processor of a computing device, a surface distance image comprising intensity values at each of a plurality of points in three dimensions, each of the intensity values corresponding to a distance from a given point in 3D space to the nearest point on the outer surface of the mammal;
   automatically determining, by the processor, a bone distance image comprising intensity values at each of a plurality of points in three dimensions, each of the intensity values of the bone distance image corresponding to a distance from a given point in 3D space to the nearest identified bone tissue of the mammal; and
   automatically detecting, by the processor, the region of interest corresponding to soft tissue interior to the mammal rib cage using the surface distance image and the bone distance image.

2. The method of claim 1, wherein the detecting step comprises:
   applying, by the processor, a threshold to the surface distance image to determine a surface distance mask corresponding to a central region of the mammal body;
   applying, by the processor, a threshold to the bone distance image to determine a bone distance mask corresponding to one or more regions at least a given distance from identified bone tissue of the mammal;
   applying, by the processor, an AND operation of the surface distance mask and the bone distance mask to identify only a region interior to the rib cage, within the region of interest; and
   applying, by the processor, a dilation operation and/or a watershed operation to expand outward a region identified following the AND operation, without encroaching the identified bone tissue, thereby detecting the region of interest interior to the mammal rib cage.

3. The method of claim 2, further comprising determining, by the processor, a transverse plane corresponding to a lower end of the rib cage.

4. The method of claim 3, wherein determining the transverse plane comprises estimating a transverse coordinate corresponding to the lower end of the rib cage from the surface distance image and the bone distance image.

5. The method of claim 2, further comprising applying a filter to the result of the AND operation to remove one or more volumes that lie outside the rib cage.

6. The method of claim 1, wherein the detecting step comprises:
   automatically determining, by the processor, a search region mask from values of distance from front (abdominal) surface to nearest bone expressed as a function of nose-to-tail z-coordinate, said search region mask identifying a volume of the mammal excluding regions of the head above the neck and excluding regions below the rib cage;
   automatically determining, by the processor, a bone distance mask using the bone distance image, wherein the bone distance mask corresponds to one or more regions at least a given distance from identified bone tissue of the mammal;
   automatically determining, by the processor, a surface distance mask using the surface distance image corresponding to one or more regions at least a given distance from the outer surface of the mammal;
   applying, by the processor, an AND operation of the search region mask, the bone distance mask, and the surface distance mask, thereby identifying a seed region interior to the rib cage, within the region of interest; and
   applying, by the processor, a dilation operation and/or a watershed operation to expand the seed region identified following the AND operation outward, without encroaching the identified bone tissue, then applying, by the processor, an AND operation of the result of the dilation and/or watershed operation with the search region mask, thereby detecting the region of interest interior to the mammal rib cage.

7. The method of claim 1, wherein the detecting step comprises:
   automatically determining, by the processor, a search region mask using values of distance from front (abdominal) surface to nearest bone expressed as a function of nose-to-tail z-coordinate, said search region mask identifying a volume of the mammal excluding regions of the head above the neck and excluding regions below the rib cage;
   automatically determining, by the processor, a bone distance mask using the bone distance image, wherein the bone distance mask corresponds to one or more regions at least a given distance from identified bone tissue of the mammal;

automatically determining, by the processor, a composite distance image computed as the difference between the surface distance image and the bone distance image;

applying, by the processor, a threshold to the composite distance image to determine a composite distance mask;

applying, by the processor, an AND operation of the search region mask, the bone distance mask, and the composite distance mask, thereby identifying a seed region interior to the rib cage, within the region of interest; and applying, by the processor, a dilation operation and/or a watershed operation to expand the seed region identified following the AND operation outward, without encroaching the identified bone tissue, then applying, by the processor, an AND operation of the result of the dilation and/or watershed operation with the search region mask, thereby detecting the region of interest interior to the mammal rib cage.

8. The method of claim 1, wherein the detecting step comprises:

automatically determining, by the processor, a bone distance mask using the bone distance image, wherein the bone distance mask corresponds to one or more regions at least a given distance from identified bone tissue of the mammal;

automatically determining, by the processor, a composite distance image computed as the difference between the surface distance image and the bone distance image;

applying, by the processor, a threshold to the composite distance image to determine a composite distance mask;

applying, by the processor, an AND operation of the bone distance mask and the composite distance mask, thereby identifying an intermediate result; and automatically determining, by the processor, using the composite distance mask, a transverse plane corresponding to a lower end of the rib cage, and removing from the intermediate result all volumes below said transverse plane, thereby identifying a seed region interior to the rib cage, within the region of interest, then applying, by the processor, a dilation operation and/or a watershed operation to expand the resulting seed region outward, without encroaching the identified bone tissue, thereby detecting the region of interest interior to the mammal rib cage.

9. A method for automatically detecting a region of interest in a 3D image of a mammal corresponding to soft tissue largely or exclusively interior to the mammal rib cage, the method comprising:

at least one of (a) and (b), as follows:

(a) automatically determining using the 3D image of the mammal, by a processor of a computing device, a surface distance image comprising intensity values at each of a plurality of points in three dimensions, each of the intensity values corresponding to a distance from a given point in 3D space to the nearest point on the outer surface of the mammal, and applying, by the processor, a threshold to the surface distance image to determine a surface distance mask corresponding to a central region of the mammal body;

(b) automatically determining using the 3D image of the mammal, by the processor of the computing device, a body mask corresponding to mammal body, and applying an erosion operation to the body mask to obtain a surface distance mask equivalent;

and at least one of (c) and (d), as follows:

(c) automatically determining using the 3D image of the mammal, by the processor, a bone distance image comprising intensity values at each of a plurality of points in three dimensions, each of the intensity values of the bone distance image corresponding to a distance from a given point in 3D space to the nearest identified bone tissue of the mammal, and applying, by the processor, a threshold to the bone distance image to determine a bone distance mask corresponding to one or more regions at least a given distance from identified bone tissue of the mammal;

(d) automatically determining using the 3D image of the mammal, by the processor, a bone mask corresponding to bone tissue, and applying a dilation operation to the bone mask to obtain a bone distance mask equivalent; and automatically detecting, by the processor, the region of interest corresponding to soft tissue interior to the mammal rib cage using (i) at least one of the surface distance mask and the surface distance mask equivalent, and (ii) at least one of the bone distance mask and the bone distance mask equivalent.

10. The method of claim 9, further comprising determining, by the processor, a transverse plane corresponding to a lower end of the rib cage.

11. The method of claim 10, wherein determining the transverse plane comprises estimating a transverse coordinate corresponding to the lower end of the rib cage from the surface distance image and the bone distance image.

12. The method of claim 9, wherein the detecting step comprises:

automatically determining, by the processor, a search region mask from values of distance from front (abdominal) surface to nearest bone expressed as a function of nose-to-tail z-coordinate, said search region mask identifying a volume of the mammal excluding regions of the head above the neck and excluding regions below the rib cage;

applying, by the processor, an AND operation of the search region mask, the bone distance mask (or bone distance mask equivalent), and the surface distance mask (or surface distance mask equivalent), thereby identifying a seed region interior to the rib cage, within the region of interest; and applying, by the processor, a dilation operation and/or a watershed operation to expand the seed region identified following the AND operation outward, without encroaching the identified bone tissue, then applying, by the processor, an AND operation of the result of the dilation and/or watershed operation with the search region mask, thereby detecting the region of interest interior to the mammal rib cage.

13. The method of claim 12, further comprising applying a filter to the result of the AND operation to remove small distinct regions smaller than a determined threshold volume.

14. The method of claim 9, wherein the detecting step comprises:

automatically determining, by the processor, a search region mask using values of distance from front (abdominal) surface to nearest bone expressed as a function of nose-to-tail z-coordinate, said search region mask identifying a volume of the mammal excluding regions of the head above the neck and excluding regions below the rib cage;

automatically determining, by the processor, a composite distance image computed as the difference between the surface distance image and the bone distance image;

applying, by the processor, a threshold to the composite distance image to determine a composite distance mask;

applying, by the processor, an AND operation of the search region mask, the bone distance mask, and the composite distance mask, thereby identifying a seed region interior to the rib cage, within the region of interest; and applying, by the processor, a dilation operation and/or a watershed operation to expand the seed region identified following the AND operation outward, without encroaching the identified bone tissue, then applying, by the processor, an AND operation of the result of the dilation and/or watershed operation with the search region mask, thereby detecting the region of interest interior to the mammal rib cage.

15. The method of claim 9, wherein the detecting step comprises:

automatically determining, by the processor, a composite distance image computed as the difference between the surface distance image and the bone distance image;

applying, by the processor, a threshold to the composite distance image to determine a composite distance mask;

applying, by the processor, an AND operation of the bone distance mask and the composite distance mask, thereby identifying an intermediate result; and automatically determining, by the processor, using the composite distance mask, a transverse plane corresponding to a lower end of the rib cage, and removing from the intermediate result all volumes below said transverse plane, thereby identifying a seed region interior to the rib cage, within the region of interest, then applying, by the processor, a dilation operation and/or a watershed operation to expand the resulting seed region outward, without encroaching the identified bone tissue, thereby detecting the region of interest interior to the mammal rib cage.

16. A system for detecting a region of interest in a 3D image of a mammal, the system comprising: a processor; and a memory having instructions stored thereon, wherein the instructions, when executed by the processor, cause the processor to:

(i) at least one of (a) and (b), as follows:

(a) automatically determine, using the 3D image of the mammal, a surface distance image comprising intensity values at each of a plurality of points in three dimensions, each of the intensity values corresponding to a distance from a given point in 3D space to the nearest point on the outer surface of the mammal, and apply a threshold to the surface distance image to determine a surface distance mask corresponding to a central region of the mammal body;

(b) automatically determine, using the 3D image of the mammal, a body mask corresponding to mammal body, and apply an erosion operation to the body mask to obtain a surface distance mask equivalent;

and (ii) at least one of (c) and (d), as follows:

(c) automatically determine, using the 3D image of the mammal, a bone distance image comprising intensity values at each of a plurality of points in three dimensions, each of the intensity values of the bone distance image corresponding to a distance from a given point in 3D space to the nearest identified bone tissue of the mammal, and apply a threshold to the bone distance image to determine a bone distance mask corresponding to one or more regions at least a given distance from identified bone tissue of the mammal;

(d) automatically determine, using the 3D image of the mammal, a bone mask corresponding to bone tissue, and apply a dilation operation to the bone mask to obtain a bone distance mask equivalent;

and (iii) automatically detect, by the processor, the region of interest corresponding to soft tissue interior to the mammal rib cage using (i) at least one of the surface distance mask and the surface distance mask equivalent, and (ii) at least one of the bone distance mask and the bone distance mask equivalent.

17. A non-transitory computer readable medium for detecting a region of interest in a 3D image of a mammal, the non-transitory computer readable medium having instructions stored thereon, wherein the instructions, when executed by a processor, cause the processor to:

(i) at least one of (a) and (b), as follows:

(a) automatically determine, using the 3D image of the mammal, a surface distance image comprising intensity values at each of a plurality of points in three dimensions, each of the intensity values corresponding to a distance from a given point in 3D space to the nearest point on the outer surface of the mammal, and apply a threshold to the surface distance image to determine a surface distance mask corresponding to a central region of the mammal body;

(b) automatically determine, using the 3D image of the mammal, a body mask corresponding to mammal body, and apply an erosion operation to the body mask to obtain a surface distance mask equivalent; and (ii) at least one of (c) and (d), as follows:

(c) automatically determine, using the 3D image of the mammal, a bone distance image comprising intensity values at each of a plurality of points in three dimensions, each of the intensity values of the bone distance image corresponding to a distance from a given point in 3D space to the nearest identified bone tissue of the mammal, and apply a threshold to the bone distance image to determine a bone distance mask corresponding to one or more regions at least a given distance from identified bone tissue of the mammal;

(d) automatically determine, using the 3D image of the mammal, a bone mask corresponding to bone tissue, and apply a dilation operation to the bone mask to obtain a bone distance mask equivalent; and (iii) automatically detect, by the processor, the region of interest corresponding to soft tissue interior to the mammal rib cage using (i) at least one of the surface distance mask and the surface distance mask equivalent, and (ii) at least one of the bone distance mask and the bone distance mask equivalent.

\* \* \* \* \*